United States Patent [19]

Aagard

[11] 4,322,621
[45] Mar. 30, 1982

[54] FOLDED PATH ABSORPTION CELL GAS SENSOR

[75] Inventor: Roger L. Aagard, Richfield, Minn.

[73] Assignee: Honeywell Inc., Minneapolis, Minn.

[21] Appl. No.: 146,818

[22] Filed: May 5, 1980

[51] Int. Cl.³ .......................... G01J 1/00; G01J 1/42; G02B 5/10
[52] U.S. Cl. .................................. 250/343; 250/353; 250/373; 350/293; 350/299; 356/440
[58] Field of Search .............. 250/343, 353, 373, 345, 250/575; 350/293, 299; 356/440

[56] References Cited

U.S. PATENT DOCUMENTS

| | | |
|---|---|---|
| 3,319,071 | 5/1967 | Werth et al. |
| 3,394,253 | 7/1968 | Harrick et al. ........................ 250/353 |
| 3,792,272 | 2/1974 | Harte et al. ........................... 250/343 |
| 4,111,531 | 9/1978 | Lavelle et al. ....................... 350/293 |
| 4,180,734 | 12/1979 | Gedeon ................................ 250/345 |

Primary Examiner—Alfred E. Smith
Assistant Examiner—Carolyn E. Fields
Attorney, Agent, or Firm—Omund R. Dahle

[57] ABSTRACT

In an optical absorption gas sensor there is a practical problem of obtaining a sufficiently long optical path necessary to provide the required sensitivity within a compact space. In the present invention the path length can be multiplied to about 2 meters in a hemispheric like chamber having a radius about 8 cm. A novel, compact and inexpensive cell structure for increasing the optical path length by multiple reflections is provided.

11 Claims, 5 Drawing Figures

FOLDED PATH ABSORPTION CELL GAS SENSOR

BACKGROUND AND SUMMARY OF THE INVENTION

A long optical path length is often necessary to improve the sensitivity of optical absorption gas sensors. This conflicts with the practical necessity of providing a compact product. In the present invention the path length can be multiplied to about 2 meters in a hemispheric like chamber having a radius of about 8 cm. A novel compact and inexpensive cell structure for increasing the optical path length of multiple relections is disclosed.

DESCRIPTION

Figure 1:
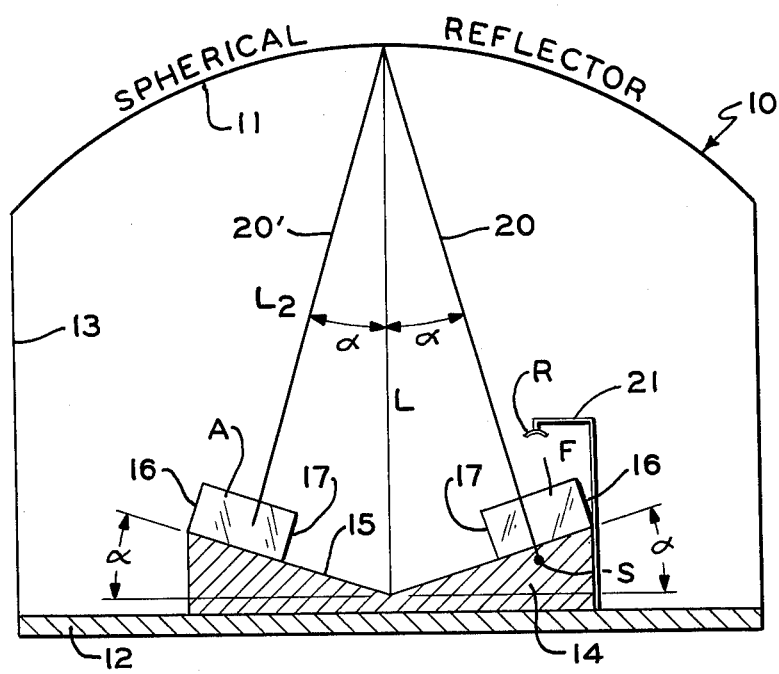
FIG. 1 is a simplified schematic side view of the interior of the gas sensor showing the spherical reflector and representative mirror sections.
Figure 3:
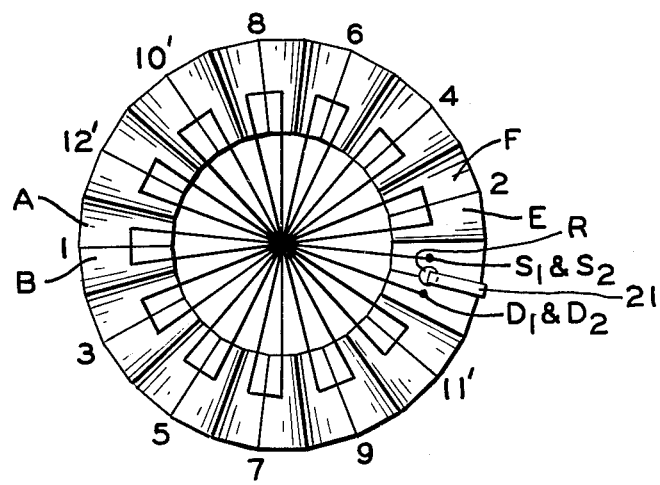
FIG. 3 is a more complete top view and diagrams the complete reflection path from light source to detector.
Figure 4:
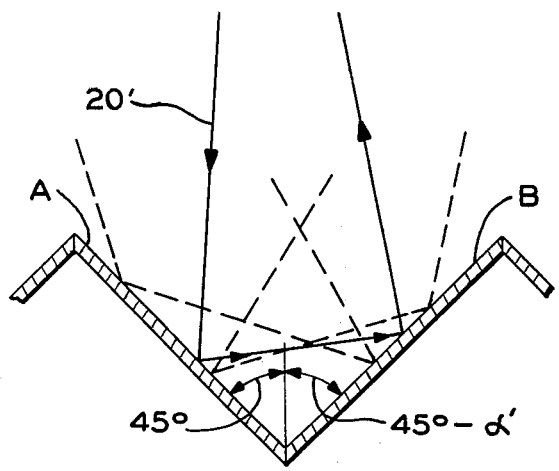
FIG. 4 is a cross-section of a mirror pair and diagrams the light beam deflection at the mirror facets; and, FIG. 5 is a block diagram of the electronic system in which the sensor is used.

Referring now to FIG. 1 there is disclosed an enclosure 10 for a folded path absorption cell gas sensor which includes a reflector or mirror portion 11 in the shape of a sector of a sphere. The spherical sector may be a hemisphere if desired in which case the section 11 of the enclosure directly joins a flat base plate section 12, or sector 11 may be smaller as shown in FIG. 1 in which case a suitable wall section 13 is used. Mounted on the base plate 12 is a center mirror means 14 (the top view of which is best seen in FIG. 3) which is axially aligned around a line L dropped perpendicular from the apex of the spherical reflector. The mirror means 14 is shown in FIG. 3 as having an annular or ring shaped perimeter area divided into 26 equal segments including twelve sets of mirror pairs equally spaced around the perimeter of means 14 together with a source segment $S_1$ and $S_2$ and a detector segment $D_1$ and $D_2$. The beam directed from the sources $S_1$ and $S_2$ to the apex of reflector 11 makes an angle $\alpha$ with the perpendicular line L. The mirror elements such as A and B or E and F of mirror pairs 1 and 2 are each elevated or canted in two axis. From FIG. 1 it is clear that the mounting surface 15 is generally sloped or elevated at an angle $\alpha$ so that the outer edge 16 of mirror elements A and F is higher than the inner edge 17. Furthermore, the faces of mirror elements (i.e. element A and B) of each mirror pair are set at an angle of $90°-\alpha'$ (oriented nearly perpendicular) to one another as shown in FIG. 4, where $\alpha' = TAN^{-1} B_2/L_2$, $L_2$ being the distance from the apex of the spherical mirror to the beam axis interception point on mirror element A and $B_2$ being half the distance between interception points on mirror elements A and B. The mirror A further makes a 45° angle to the axis of the light beam 20'. Thus in each of the mirror pairs 1-9, 10', 11' and 12, the mirror elements face each other at $90°-\alpha'$ so that the axis of a light beam from the apex of the spherical reflector falling on element A is reflected to element B and reflected again back to the apex of the spherical reflector. Instead of mirror A making a 45° angle to the axis of the light beam 20', the bisector of the angle $90°-\alpha'$ formed by the mirror pair may be directed toward the apex of the spherical reflector, if desired.

Figure 2:
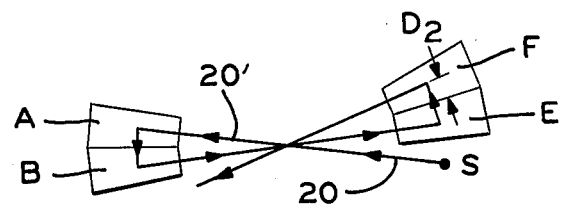
FIG. 2 is a partial top view viewing two pairs of mirror sections and diagramming the reflection path.

FIGS. 1, 2 and 3 show that a light source S ($S_1$ and $S_2$) located below the mirror plane directs a radiation (i.e. light) beam 20 to the spherical reflector 11. The source S ($S_1$ and $S_2$) may be composition tuned Infrared Light Emitting Diodes (IRLED's) or a laser source of appropriate wavelength. The use of the work light in this specification and claims is intended to include the infrared spectrum. As shown in FIGS. 2 and 3 IR radiation from the source or sources is reflected and refocused by the spherical mirror to fall on mirror section A of mirror pair 1, from mirror section A to B, from mirror section B to the spherical reflector, to mirror section E of mirror pair 2, to mirror section F, from mirror 2 to 3 etc., each time the reflective path including the spherical reflector, until the radiation progresses through mirror pair 12 and reaches the detector $D_1$. A spherical mirror R, suspended from mounting 21, intercepts a small amount of radiation from the sources and directs it to detector $D_2$ to provide a reference so that source intensity changes affect them equally.

The function of the mirror pairs is to move the effective location of the source radially so that the beam is reflected across the center of the spherical mirror. In the embodiment disclosed a multiplication of 24r is achieved, where r is the radius of the spherical reflector 11, an 8 cm radius mirror would provide about a 2 meter path length.

The light emitting diode sources have wavelengths $\lambda_1$ and $\lambda_2$ which are coincident and near, but not coincident with the absorption band of the gas to be sensed. They must be bonded to the same header or integrated as close together as possible, so that radiation from both of them will reach a detector of a reasonable size.

Figure 5:
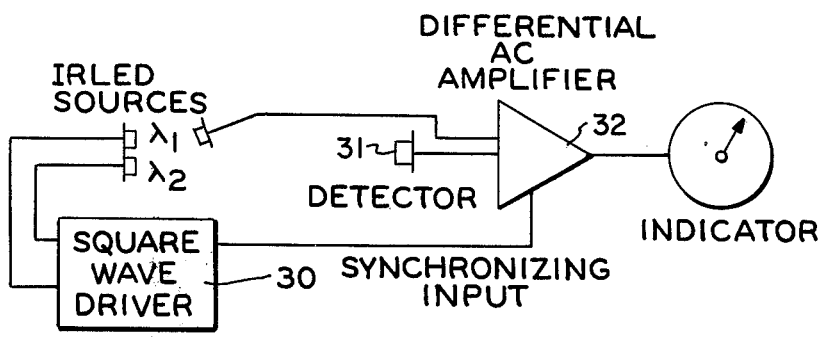

A block diagram of the sensor electronics is shown in FIG. 5. The IRLED's have center radiant emission at $\lambda_1$ and $\lambda_2$ and are alternately switched on by the square wave driver 30. When there is no gas of absorption at $\lambda_1$, in the cell, the detector 31 response for $\lambda_1$ and $\lambda_2$ is equalized and there is no AC signal at the output of the amplifier 33. Wavelengths $\lambda_1$ and $\lambda_2$ are chosen close enough together so that dust and humidity changes affect them nearly equally. The presence of a gas absorbing at $\lambda_1$ attenuates the radiation when source of $\lambda_1$ is on, and does not attenuate $\lambda_2$. Thus an AC signal will appear at the output of the amplifier of amplitude proportional to the concentration of the absorbing gas and be displayed on the indicator.

In the construction of the enclosure 10 the sources $S_1$ and $S_2$ as well as the detectors $D_1$ and $D_2$ may be protected by IR transmissive windows, if it is desirable to protect these elements from the gases flowing through the enclosure. There may be gas inlet and outlet ports (not shown) for the enclosure or the enclosure may allow free flow through it as the application requires.

The embodiments of the invention in which an exclusive right is claimed are defined as follows:

1. A folded path optical type absorption cell gas sensor comprising:
   an absorption cell gas sensor enclosure;
   a spherical shaped reflector forming part of the enclosure of the absorption cell;
   said enclosure further including a base section having mounted thereon an annular shaped mirror complex, said annular mirror complex comprising a plurality of mirror pairs, each of said mirror pairs having a first mirror element and a second mirror element, the first mirror element being set at an angle nearly perpendicular to the second mirror element in each of said mirror pairs, and wherein said mirror pairs are each generally directed towards the apex of the spherical reflector;

a source of light;

detector means;

a multifolded light beam directed from said source towards the apex of said spherical reflector and reflected therefrom onto said first mirror element of the first of said mirror pairs, reflected therefrom to the second mirror element thereof, reflected therefrom by way of spherical reflector to the first mirror element of the second mirror pair, the multifolding sequence continuing until the light beam traverses all of said plurality of mirror pairs and is finally reflected to said detector means.

2. Apparatus according to claim 1 wherein said annular mirror complex comprises twelve mirror pairs.

3. Apparatus according to claim 1 wherein the first and second mirror elements of each pair are set at an angle of $90°-\alpha'$ to each other, where $\alpha'=\mathrm{TAN}^{-1} B_2/L_2$, $L_2$ being the distance from the apex of the spherical mirror and the beam axis interception point on the mirror elements and $B_2$ being half of the distance between the beam interception points on the first and second mirror elements.

4. Apparatus according to claim 3 wherein a bisector of the angle $90°-\alpha'$ formed by said mirror pair elements is directed towards the apex of the spherical reflector.

5. Apparatus according to claim 1 wherein said spherical shaped reflector is hemispherical.

6. Apparatus according to claim 1 wherein said spherical shaped reflector is a small sector of a sphere.

7. A folded path absorption cell gas sensor comprising:

a source of infrared light;

a detector of infrared light;

a circle of mirror parts comprising a plurality of mirror pairs, said circle of mirror pairs being mounted on the base of an absorption cell gas sensor chamber, each of said mirror pairs consisting of two planar mirrors, one mirror nearly perpendicular to the other, said two mirrors having a common edge, one mirror being a receiving mirror and the other a reflecting mirror;

a spherical reflector forming an upper portion of said gas sensor chamber, each of said mirror pairs having an axial orientation towards the apex of said spherical reflector;

said light from said source being directed towards said reflector apex and reflected therefrom to the receiving mirror of the first mirror pair of said circle of mirror pairs, the resulting light reflected from the reflecting mirror of said first pair being directed toward said reflector apex and reflected therefrom to the receiving mirror of the second mirror pair of said circle of mirror pairs and continuing in like order to the ultimate of the plurality of mirror pairs whereupon the resulting light reflected from the reflecting mirror of said ultimate pair is directed towards said reflector apex and reflected therefrom to said infrared detector, thereby providing a relatively long light path from source to detector in a compact enclosure.

8. Apparatus according to claim 7 wherein said circle of mirror pairs comprises at least 8 mirror pairs.

9. Apparatus according to claim 7 wherein said circle of mirror pairs comprises twelve mirror pairs.

10. Apparatus according to claim 7 wherein the two planar mirrors of each mirror pair are set at an angle of $90°-\alpha'$ to each other, where $\alpha'=\mathrm{TAN}^{-1} B_2/L_2$, $L_2$ being the distance from the apex of the spherical mirror to the beam axis interception point on the planar mirror and $B_2$ being one half the distance between the beam interception points on the two planar mirrors of a pair.

11. Apparatus according to claim 10 wherein a bisector of the angle $90°-\alpha'$ formed by the two planar mirrors is directed toward the apex of the spherical reflector.

* * * * *